United States Patent
Penny

(10) Patent No.: US 11,317,980 B2
(45) Date of Patent: May 3, 2022

(54) INSTRUMENT END EFFECTOR IDENTIFICATION

(71) Applicant: Asensus Surgical US, Inc., Durham, NC (US)

(72) Inventor: Matthew R Penny, Holly Springs, NC (US)

(73) Assignee: ASENSUS SURGICAL US, INC., Durham, NC (US)

( * ) Notice: Subject to any disclaimer, the term of this patent is extended or adjusted under 35 U.S.C. 154(b) by 36 days.

(21) Appl. No.: 15/975,765

(22) Filed: May 9, 2018

(65) Prior Publication Data

US 2021/0307852 A1    Oct. 7, 2021

Related U.S. Application Data

(60) Provisional application No. 62/503,360, filed on May 9, 2017.

(51) Int. Cl.
*A61B 34/00* (2016.01)
*A61B 46/10* (2016.01)
*A61B 34/30* (2016.01)

(52) U.S. Cl.
CPC .............. *A61B 34/70* (2016.02); *A61B 34/30* (2016.02); *A61B 46/10* (2016.02)

(58) Field of Classification Search
CPC .......... A61B 34/30; A61B 90/98; A61B 34/70
See application file for complete search history.

(56) References Cited

U.S. PATENT DOCUMENTS

| 2016/0361127 A1* | 12/2016 | Dachs, II | A61B 46/40 |
| 2017/0203118 A1* | 7/2017 | Chang | A61B 18/14 |

FOREIGN PATENT DOCUMENTS

| WO | 9220295 | 11/1992 |
| WO | WO 2015/142889 | * 9/2015 |

* cited by examiner

*Primary Examiner* — Thomas McEvoy

(57) ABSTRACT

A mechanical assembly is used to communicate to a robotic system information about a type of instrument mounted to a robotic manipulator arm. The assembly includes a sensor and a receiving component on the robotic manipulator arm. The receiving component includes a member moveable relative to said at least one sensor. A first surgical instrument is attachable to the robotic manipulator arm and is provided with a first mechanical identification feature positioned to cause movement of the moveable member relative to the sensor, causing a first response at the sensor. A second surgical instrument is similarly attachable, but causes a second response at the sensor that differs from the first response. This allows the robotic system to determine instrument type based on the response of the sensor from attachment of an instrument.

10 Claims, 3 Drawing Sheets

INSTRUMENT END EFFECTOR IDENTIFICATION

This application claims the benefit of U.S. Provisional Application No. 62/503,360, filed May 9, 2017.

BACKGROUND

There are various types of surgical robotic systems on the market or under development. Some surgical robotic systems use a plurality of robotic arms. Each arm carries a surgical instrument, or the camera used to capture images from within the body for display on a monitor. See U.S. Pat. No. 9,358,682 and US 20160058513. Other surgical robotic systems use a single arm that carries a plurality of instruments and a camera that extend into the body via a single incision. See WO 2016/057989. Each of these types of robotic systems uses motors to position and/or orient the camera and instruments and to, where applicable, actuate the instruments. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

Some surgical and industrial robotic systems are configured to interchangeably receive a variety of end effectors. Different end effectors might possess different dimensions, geometry, weight characteristics, jaw open-close ranges, etc. For this reason, when an end effector is mounted to a robotic manipulator, the system can most optimally move and actuate the end effector if the system has been given input as to the characteristics of the end effector. This application describes a system and method for giving input to the surgical robotic system relating to the type of end effector that has been mounted.

DETAILED DESCRIPTION

Figure 1:
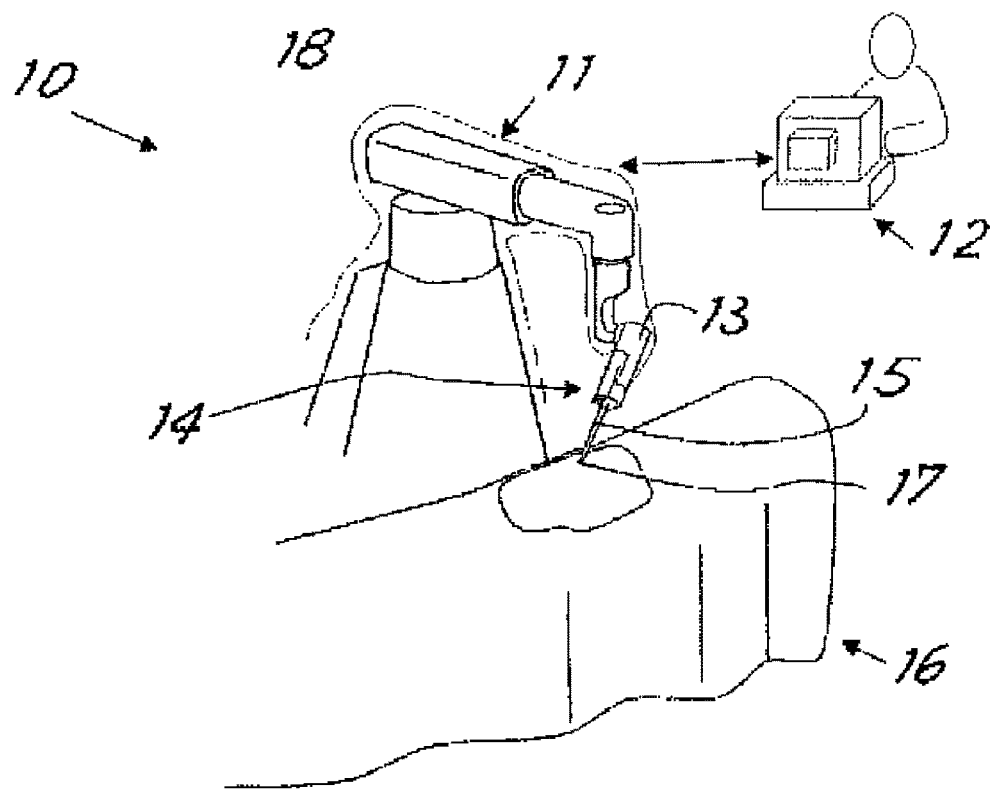
FIG. 1 schematically illustrates a robotic manipulator of a type used in robotic surgical procedures.

FIG. 1 shows components of a robotic surgical system 10 of the type described in U.S. Pat. No. 9,358,682 and US 20160058513. Features of the system 10 are shown to facilitate an understanding of the way in which the concepts of the present invention may be implemented, but it should be understood that the invention may be used with a variety of different surgical or industrial robotic systems and is not limited to use with system 10.

System 10 comprises at least one arm 11. This arm may be a robotic manipulator arm which operates under the control of a command console 12 operated by the surgeon, as described in the Background, although in alternative embodiments having robotic functionality of the instruments but not robotic arms, it might be a support arm that does not have robotic capabilities. In this description, the arm described is one capable of robotic motion.

The arm 11 (or each arm) has a terminal portion 13 designed to support and operate a surgical device assembly 14. The surgical device assembly includes a surgical instrument having shaft 15 and a distal end effector 17 positionable within a patient 16.

Figure 2:
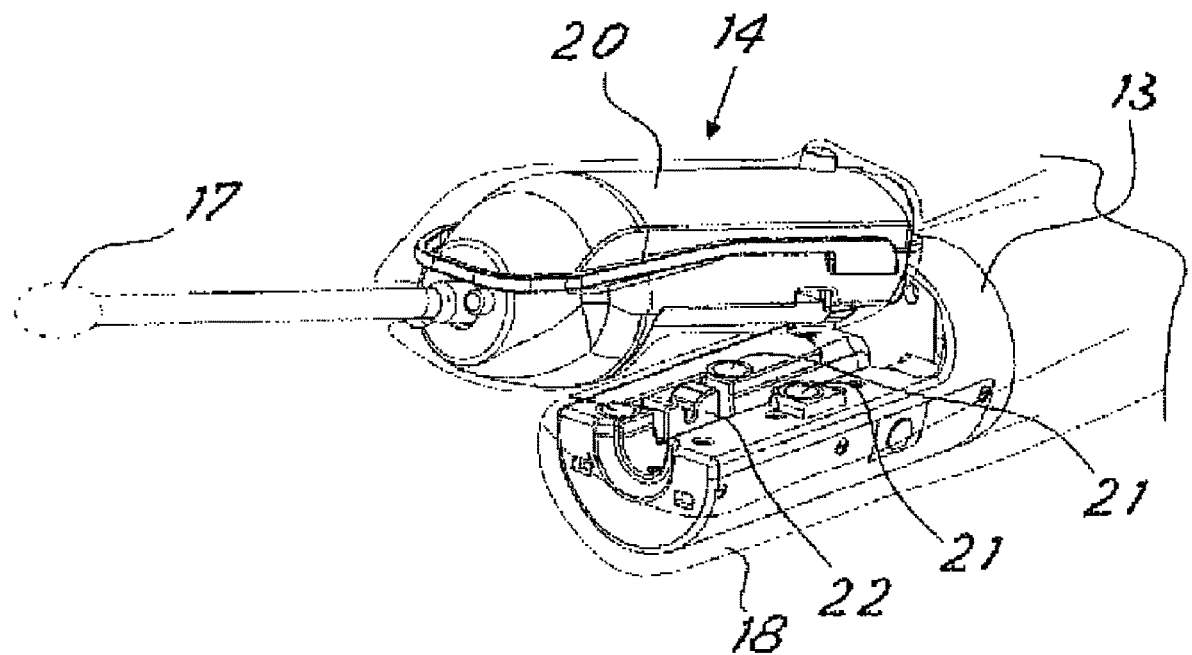
FIG. 2 illustrates the step of mounting of a surgical device onto the manipulator of FIG. 1.

In this configuration, the manipulator arm receives the surgical device assembly 14 at the terminal portion 13 as shown in FIG. 2. The surgical device assembly includes a proximal housing 20 that is received by the terminal portion 13 as shown.

The end effector 17 may be one of many different types of that are used in surgery including, without limitation, end effectors 17 having one or more of the following features: jaws that open and close, section at the distal end of the shaft that bends or articulates in one or more degrees of freedom (the articulation occurring at discrete joints or on a flexible continuum shaft), a tip that rolls axially relative to the shaft 15, a shaft that rolls axially relative to the manipulator arm 11. For the sake of simplicity, in FIG. 2 the end effector 17 is shown as an oval form in broken lines. The system includes instrument actuators for driving the motion of the end effector 17. These actuators, which might be motors or other types of actuators (e.g. hydraulic/pneumatic), are positioned in the terminal portion 13 of the robotic manipulator, or in the housing 20 of the surgical device assembly, or some combination of the two. In the latter example, some motion of the end effector might be driven using one or more motors in the terminal portion 13, while other motion might be driven using motors in the housing 20.

During use, the robotic system controls movement of the robotic manipulator and movement of the end effector (e.g. jaw open/close, tip roll, articulating or bending, etc.) based on surgeon input received by the system via the console 12. The control signals used to generate the various types of movement depend in some cases on the geometry, length, weight, or other parameters of the surgical instrument 14.

Figure 3:
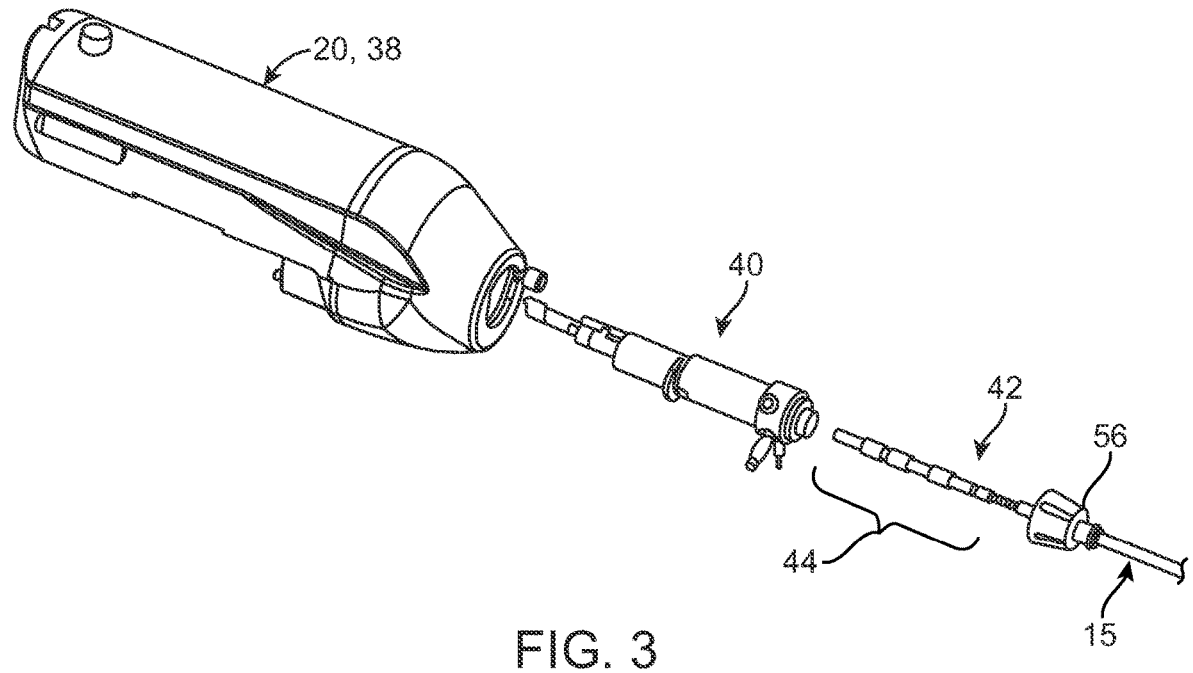
FIG. 3 is an exploded view illustrating components of the surgical device of FIG. 2.

A configuration that allows a system to receive input that allows it to know the type of surgical instrument that has been mounted to the surgical system will next be described with reference to FIG. 3. In general, the system includes a receiving component 40, and a surgical instrument 42. The surgical instrument 42 includes, at its distal end, the end effector 17 (not shown) of the surgical instrument. It also includes the shaft 15 of the surgical instrument, and drive elements 44 that are moveable to drive the elements of the shaft 15 that cause actuation (e.g. jaw open/close, tip roll, articulating or bending, etc.) of the end effector 17.

Figure 4:
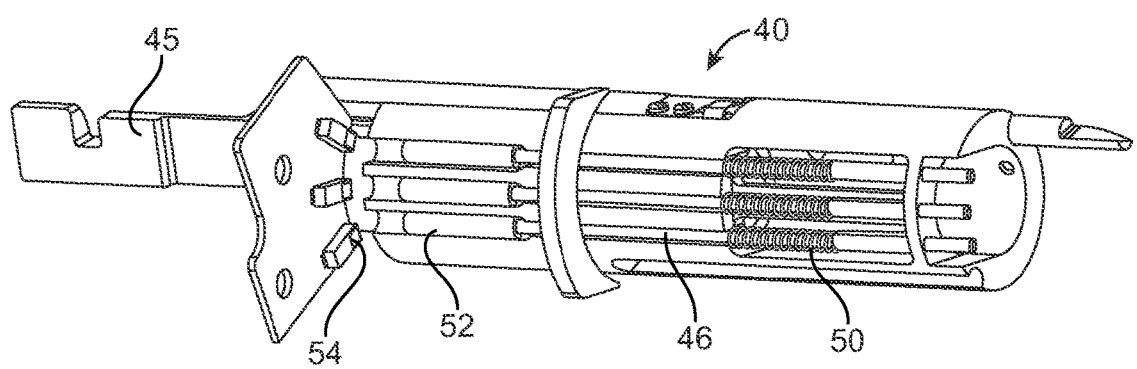
FIG. 4 shows internal features of the intermediate element of the surgical device of FIG. 3 together with the arrangement of reed switches housed within the proximal housing.

The receiving component 40 removably receives the surgical instrument 42. Referring to FIG. 4, the receiving component 40 includes a plurality of instrument identification members 46 that are slidable relative to the body 48 of the receiving component 40. These members 46 carry magnetic elements at their proximal ends 52. A plurality of sensors 54, which in this embodiment are reed switches, are positioned proximal to the members 46.

When no surgical instrument 42 is engaged with the receiving component, springs 50 bias the members 46 in a distal direction, away from the reed switches (although this could be reversed in modified embodiments). In this state, the members 46 are located to position the magnets far enough from the reed switches to prevent them from changing state. When an instrument 42 is coupled to the receiving component 40, one or more features on the instrument 42 will push on one or more members 46. When a member is pushed, the magnet at its proximal end moves closer to the corresponding magnetic reed switch. When the magnet is within the switch operating range, the switch will change states, either opening or closing a circuit. The system software identifies which of the circuits are opening or closed and can identify which instrument is engaged with the system. When the instrument 42 is removed from the system, the springs 50 act to remove the magnet from the switch operating range, changing the state of the switch back to its original state. When a different instrument is then engaged with the system, its features press a different combination of the instrument identification members 46, allowing the system to identify the instrument.

The features on the instrument 42 that depress the tissue identification members 46 may be part of a collar 56 or some other mechanical elements oriented to be in alignment with select ones of the members 46 when the instrument 42 is assembled to the receiving component 40.

Figure 5A:
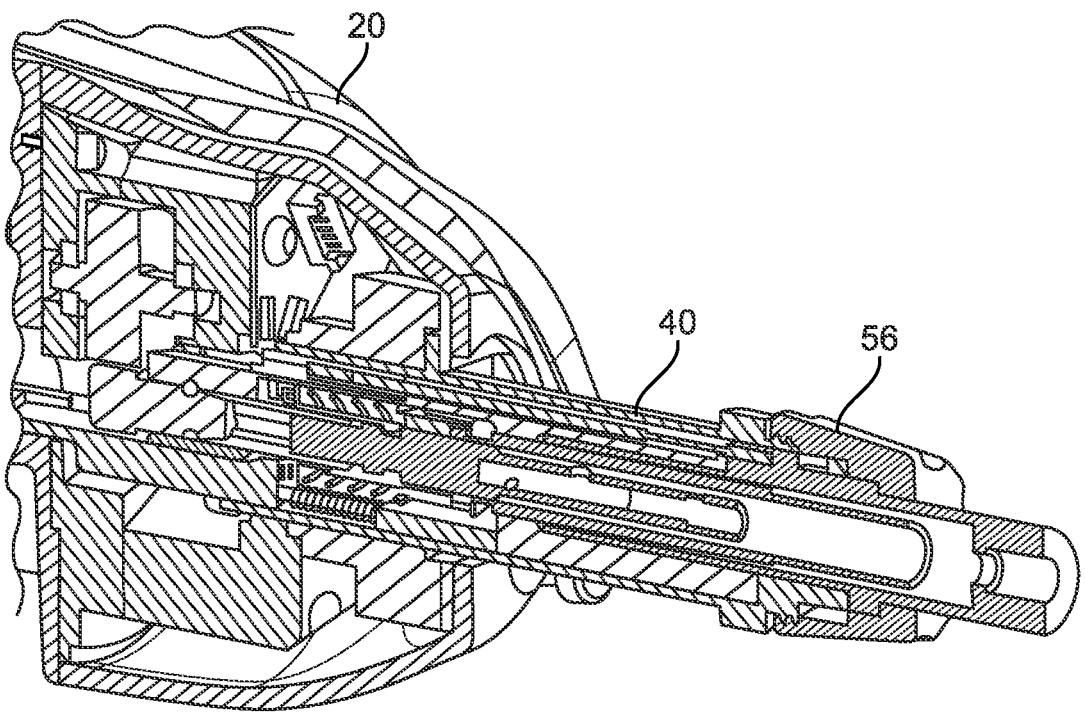
FIGS. 5A and 5B each show a cross-section view of a distal part of the proximal housing assembled with the intermediate element and the proximal part of the instrument.
Figure 5B:
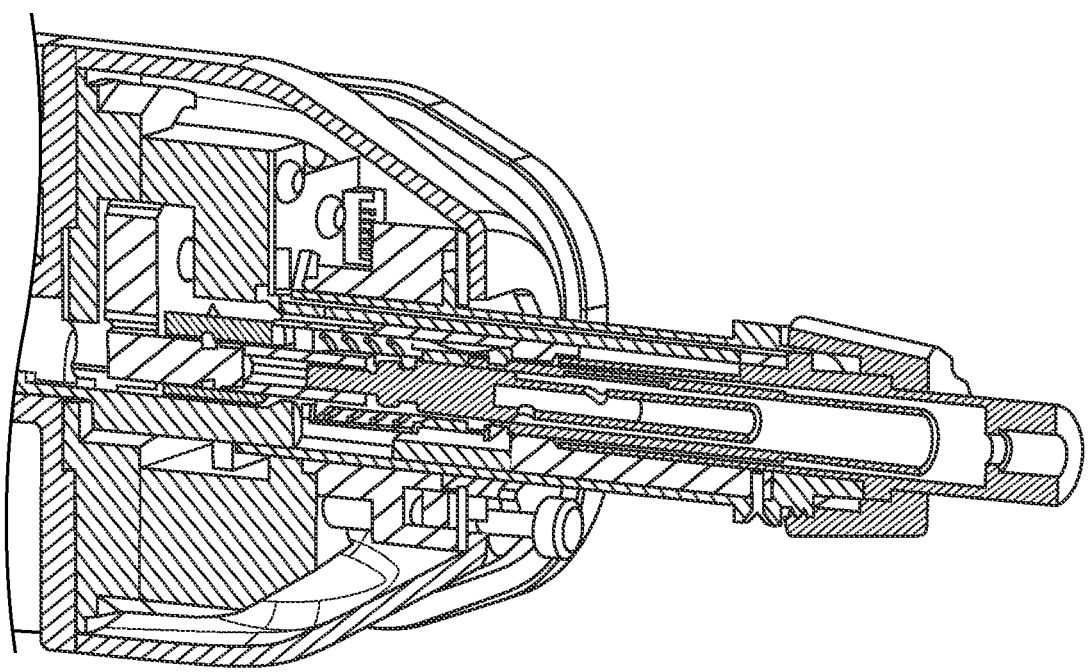

In FIG. 5A, the instrument lacks a pin populating the hole in the collar 56. This means that the recognition pin/identification member 46 on the intermediate element remains extended such that the magnet does not cause the reed switch to trigger. In FIG. 5B, collar 56 has a pin populating the hole, such that engaging the instrument with the intermediate member results in displacement of the instrument recognition pin/identification member 46 to where the magnet approaches the reed switch location, triggering the red switch. In an embodiment using three reed switches, eight unique states may be identified, corresponding to seven types of instruments and 1 "no instrument" state.

The embodiment above illustrates a series of three pins or members 46, which provide eight unique combinations of circuits opened or closed. Fewer members 46 would provide fewer unique combinations, while more members 46 will provide many more unique combinations.

The location of the sensors 54 depends on the overall configuration of the instrument assembly. In the present embodiment, as shown in FIG. 3, the assembly includes a first component 38 which is the housing 20 described above, and the sensors/reed switches 54 are housed in housing 20 which, as discussed above, is removable from the robotic manipulator. In this embodiment the receiving component 40 additionally serves to transmit motion generated by the instrument actuators to the drive elements 44 of the surgical instrument 42. More particularly, one or more mechanical transmission elements 45 (FIG. 4) of the receiving component receive mechanical output generated by the instrument actuators positioned in manipulator arm and/or housing 20 and transfers that motion to the drive elements 44 (FIG. 3). In this configuration, the robotic manipulator may be a non-sterile component covered by a drape. The housing 20 may be a non-sterile component (particularly if it houses motor actuators and/or electronic components) enclosed within a sterile drape/bag, and the surgical instrument 42 and receiving component may be sterile components. This arrangement allows surgical instruments 42 to be removed from the system and replaced with other surgical instruments while preserving sterility. For example, one instrument 42 may be removed from the receiving component 40 and replaced with another instrument 42 while the receiving component 40 remains in its position inserted within the proximal housing 20.

It should be understood that the components may be arranged in ways other than the way in which they are shown in the attached drawings. For example, the sensor(s) housed in the first component 38 (and, optionally, other features described with respect to the housing 20) can be part of the robotic manipulator and are not removeable from it. As another example, both the sensors and the features of the receiving component may be integral with the robotic manipulator, with the surgical instrument being the only removable component. As a third example, the instrument recognition features of the receiving component may be integral with the housing 20.

Alternative types of sensors may be used in place of the disclosed reed switches. For example, an alternative instrument-identification embodiment would use spring loaded pins/members 46 similar to those described above, but would be configured so that movement of the pins/members physically closes corresponding circuits instead of using magnets and magnetic reed switches as the sensors. For example, the circuit may consist of a leaf spring with one end that is connected to either power or ground and the other end elevated above the opposite electrical contact. When the spring-loaded member contacts the leaf spring, it forces the leaf spring to make electrical contact with the second pad—completing the circuit. This is a physical embodiment of what is happening inside the magnetic reed switches described in the first embodiment.

In both the first and second embodiments, the circuit does not run through the spring-loaded members 46 and as such, the members need not be made of an electrically conductive material.

A third embodiment might include an electrically conductive member/pin. When engaged with electrically active elements in the housing 20, the pin would make physical contact with either a ground or power wire. When the spring loaded pin 46 is depressed by the instrument 42, the pin would also make contact with the opposite side of the circuit—resulting in a circuit that completes itself with the spring-loaded pin.

A fourth embodiment does not require multiple circuits. In the previous embodiments, each circuit was providing a single digital value—On or Off. If the circuits provided an analog signal instead, then each analog signal can be monitored for changes in the analog value to identify instrument engagement with the system. Consider one analog sensor—a linear potentiometer for example. If the mechanical identifier on each instrument has a different length—when each instrument is engaged with the system, the spring loaded pin(s) would travel different distances when depressed. If the spring loaded pin is mated with a linear potentiometer, the different travel distances could be recognized and used as instrument identification.

In a scenario where two or more analog sensors are used, the combination of these signals may be used in a similar manner as the digital sensors described above. For example, if one analog signal can be divided up into four different ranges—it can be used to sense four different instrument configurations. When paired with another equivalent sensor, and the combinations are increased to sixteen different readings.

All prior patents and applications referred to herein, including for purposes of priority, are incorporated herein by reference.

What is claimed is:

1. A system for communicating to a robotic system information about a type of instrument mounted to a robotic manipulator arm, the system comprising:
   a robotic manipulator arm;
   a plurality of sensors on the robotic manipulator arm;
   a receiving component removably positioned on the robotic manipulator arm, the receiving component including an elongate body and a plurality of members positioned on the body, each of said members moveable relative to at least one of said plurality of sensors;
   a first instrument having
      a first distal shaft,
      a first end effector on a distal end of the first distal shaft, and
      a first collar positioned on a proximal end of the first distal shaft, the first collar including a cavity and one or more first pins within the cavity, wherein the first collar is removably mountable to the receiving component with a portion of the elongate body disposed within the cavity;
   a second instrument having
      a second distal shaft,
      a second end effector on a distal end of the second distal shaft, and
      a second collar positioned on a proximal end of the second distal shaft, the second collar including a cavity and one or more second pins within the cavity, wherein the second collar is removably mountable to the receiving component with a portion of the elongate body disposed within the cavity;
   wherein each first pin is positioned to cause movement of at least one of said plurality of members in response to mounting of the first collar to the receiving component to cause a first response at at least one of said plurality of sensors;
   wherein each second pin is positioned to cause movement of at least one of said plurality of members in response to mounting of the second collar to the receiving component to cause a second response at at least one of said plurality of sensors, wherein the first response is different from the second response; and
   wherein the robotic system is configured to determine an instrument end effector type based on the response of the at least one sensor from attachment of an instrument.

2. The system of claim 1, wherein:
   wherein the first pins are arranged such that mounting the first collar to the receiving member causes movement of a first set of one or more of the members,
   wherein the second pins are arranged such that mounting the second collar to the receiving member causes movement of a second set of one or more of the members, and
   wherein the first set and the second set include a different number of members.

3. The system of claim 2, wherein:
   the plurality of sensors are a plurality of reed switches;
   each member is moveable relative to a corresponding one of the reed switches, each member including a magnet;
   the members are positioned such that movement of the first set of one or more members in response to mounting the first collar on the receiving component causes a change of state on a first set of one or more of the reed switches;
   the members are positioned such that movement of the second set of one or more members in response to mounting the second collar on the receiving component causes a change of state on a second set of one or more of the reed switches, the first set of reed switches and the second set of reed switches comprising different numbers of reed switches.

4. The system of claim 1 wherein each member is longitudinally slidable between a first position and a second position, each member closer to a corresponding one of the plurality of sensors when in the first position than when in the second position.

5. The system of claim 4, wherein the members are biased in the second position.

6. The system of claim 1, wherein:
   the plurality of sensors are a plurality of switches;
   each member is moveable relative to a corresponding one of the switches;
   the members are positioned such that movement of a first set of one or more members in response to mounting the first collar on the receiving component causes closing of a first set of one or more of the switches using physical contact;
   the members are positioned such that movement of a second set of one or more members in response to mounting the second collar on the receiving component causes closing of a second set of the one or more of the switches using physical contact.

7. The system of claim 1, wherein:
   the plurality of sensors are a plurality of circuits;
   each member is a conductive member moveable relative to a corresponding one of the circuits to close said corresponding one of the circuits.

8. The system of claim 1, wherein:
   the plurality of sensors are an analog sensor;
   at least one of the members is moveable from a first position, in which a corresponding analog sensor is caused to deliver a first signal, to a second position in which the corresponding analog sensor is caused to deliver a second signal;
   mounting of the first collar to the receiving component causes movement of the at least one member to the first position to cause the first signal;
   mounting of the second collar to the receiving component causes movement of the at least one member to the second position to cause the second signal.

9. The system of claim 1, wherein
   the first surgical instrument includes first mechanical actuation elements;
   the second surgical instrument includes second mechanical actuation elements;
   wherein when the first surgical instrument, manipulator arm and receiving component are assembled, drive elements of the receiving component are arranged to receive drive motion from actuators and transfer the drive motion to the first actuation elements of the first surgical instrument; and
   wherein when the second surgical instrument, manipulator arm and receiving component are assembled, drive elements of the receiving component are arranged to receive drive motion from the actuators and transfer the drive motion to the second actuation elements of the second surgical instrument.

10. The system of claim 1, wherein:
    wherein the first pins are arranged such that mounting the first collar to the receiving member causes movement of one of the members by a first distance, wherein the second pins are arranged such that mounting the second collar to the receiving member causes movement of one of the members by a second distance, and wherein the first distance and the second distance are different distances.

\* \* \* \* \*